United States Patent [19]
Palestrant

[11] Patent Number: 5,336,192
[45] Date of Patent: Aug. 9, 1994

[54] SELF-SEALING VALVE DEVICE FOR ANGIOGRAPHIC CATHETERS

[76] Inventor: Aubrey M. Palestrant, 6800 N. 47th St., Paradise Valley, Ariz. 85253

[21] Appl. No.: 800,610

[22] Filed: Nov. 27, 1991

[51] Int. Cl.⁵ .......................................... A61M 5/178
[52] U.S. Cl. .................................. 604/167; 604/200; 604/202; 604/205; 604/206; 604/237; 604/241; 604/244; 604/280; 604/283; 128/912; 128/917
[58] Field of Search ................. 128/912, 917; 604/167, 604/169, 200, 202-206, 214-216, 236-237, 241, 244, 280-283; 137/844, 846; 251/149.1, 149.2, 149.4, 149.5; 141/346, 348-350

[56] References Cited

U.S. PATENT DOCUMENTS

| | | |
|---|---|---|
| 3,601,151 | 8/1971 | Winnard . |
| 3,837,381 | 9/1974 | Arroyo ................... 141/350 |
| 4,000,739 | 1/1977 | Stevens .................. 604/167 |
| 4,143,853 | 3/1979 | Abramson ............... 251/149 |
| 4,243,034 | 1/1981 | Brandt . |
| 4,261,357 | 4/1981 | Kontos ................... 604/167 |
| 4,387,879 | 6/1983 | Tauschinski ........... 251/149.1 |
| 4,424,833 | 1/1984 | Spector et al. .......... 137/849 |
| 4,430,081 | 2/1984 | Timmemans ............ 604/167 |
| 4,573,978 | 3/1986 | Reilly .................... 604/240 |
| 4,610,665 | 9/1986 | Matsumoto et al. ..... 604/167 |
| 4,626,245 | 12/1986 | Weinstein ............... 604/167 |
| 4,673,393 | 6/1987 | Suzuki et al. ........... 604/167 |
| 4,758,225 | 7/1988 | Cox et al. ............... 604/107 |
| 4,765,588 | 8/1988 | Atkinson ................ 251/149.1 |
| 4,842,591 | 6/1989 | Luther ................... 604/283 |
| 4,935,010 | 6/1990 | Cox et al. ............... 604/167 |
| 5,062,836 | 11/1991 | Wendell ................. 604/167 |
| 5,156,596 | 10/1992 | Balbierz et al. ........ 604/167 |
| 5,167,648 | 12/1992 | Jepson et al. ........... 604/283 |
| 5,215,538 | 6/1993 | Larkin .................. 251/149.1 |

FOREIGN PATENT DOCUMENTS 2019219 10/1979 United Kingdom ............ 604/283
2067075 1/1980 United Kingdom .

OTHER PUBLICATIONS

Medi-tech, Incorporated promotional brochure for "FloSwitch HP", bearing 1986 copyright notice.
Widlus, "Technical Note: Safety of High Pressure Injections Through a Flow Switch Stopcock"; Cardio Vascular and Interventional Radiology, Springer-Verlag, New York 1988.
January, 1988 catalog listing for "Hemostasis Valves" published by Cordis Corporation of Miami, Fla., p. 102.
Jan., 1988 catalog listing for "Catheter Sheath Introducer" published by Cordis Corporation of Miami, Fla., p. 97.

Primary Examiner—Randall L. Green
Assistant Examiner—P. Zuttarelli
Attorney, Agent, or Firm—Cahill, Sutton & Thomas

[57] ABSTRACT

A self-sealing valve device for an angiographic catheter includes a housing having a first end adapted to form a luer lock connection with the proximal end of the angiographic catheter. A central bore extends between the first end of the housing and an opposing second end, and a deformable elastomeric slit seal is supported across the central bore to selectively seal the proximal end of the catheter. The slit seal is adapted to permit a guidewire to be passed therethrough and advanced into the catheter while sealingly engaging the walls of the guidewire to prevent blood loss through the catheter. The second end of the housing is provided with a female luer lock connection fitting for receiving the conical tip of a syringe, stopcock, or the like, and forming a pressure-tight connection therebetween. The insertion of the conical tip of the syringe into the second end of the housing automatically deforms the slit seal for allowing fluid to pass freely therethrough, while again sealing the proximal end of the catheter when the conical tip of the syringe is removed.

20 Claims, 2 Drawing Sheets

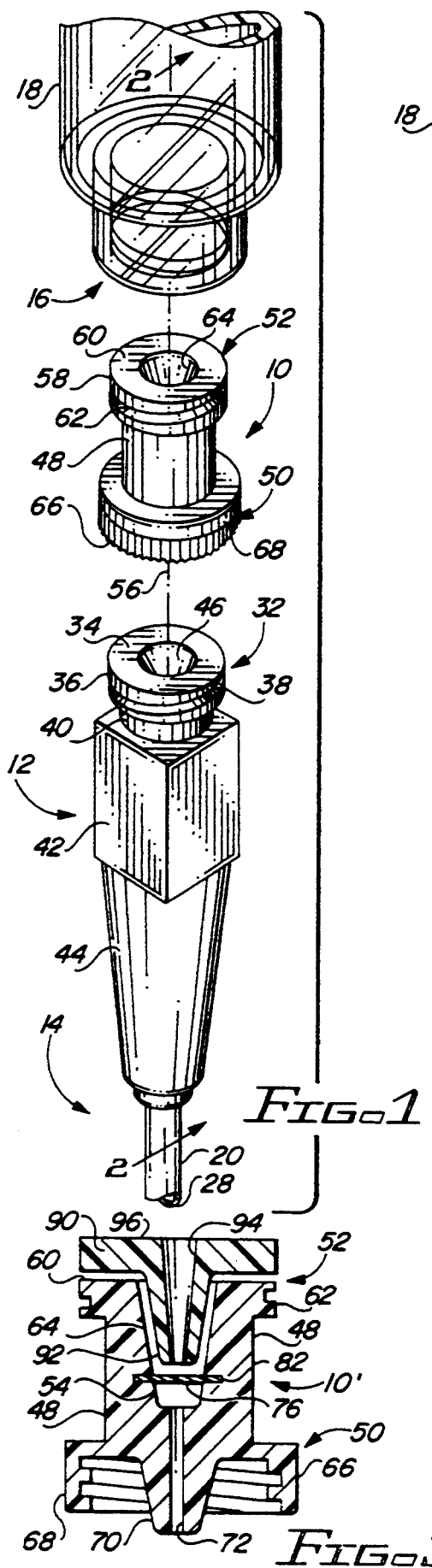
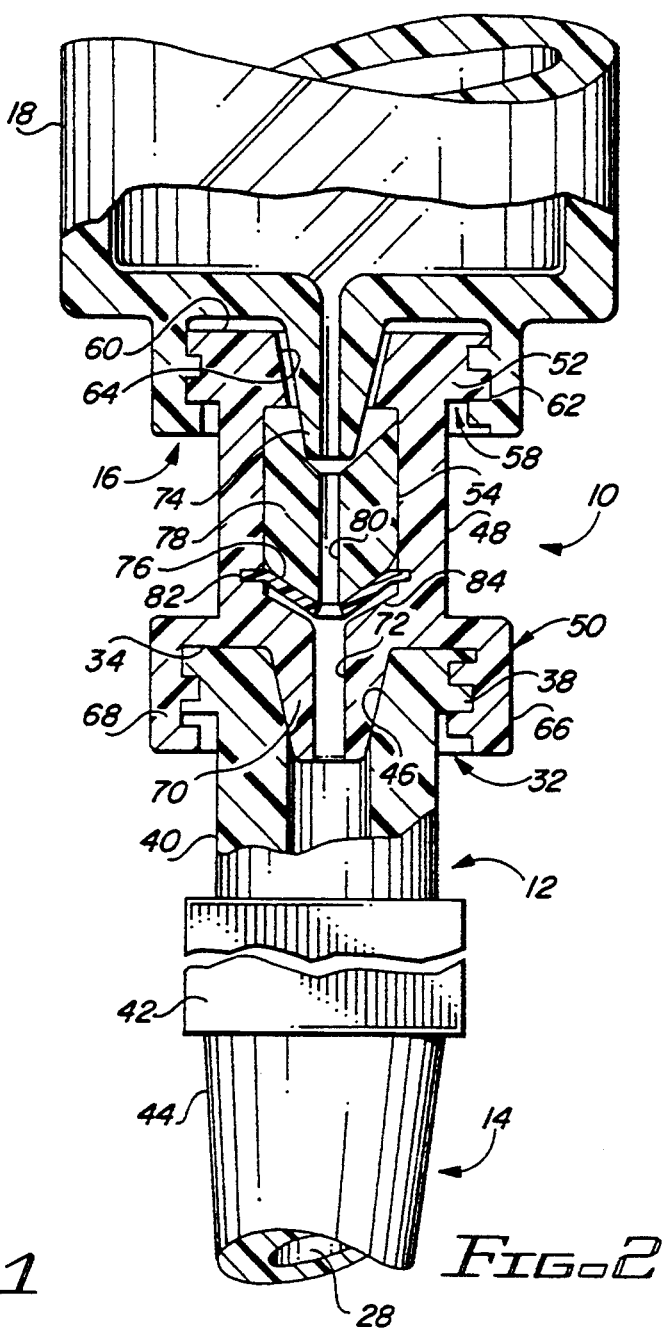
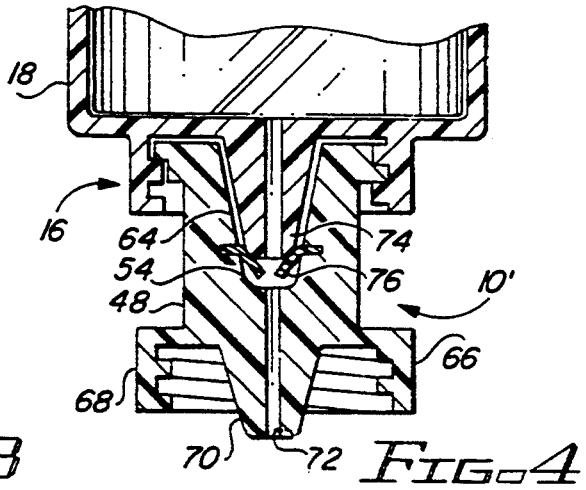

SELF-SEALING VALVE DEVICE FOR ANGIOGRAPHIC CATHETERS

BACKGROUND OF THE INVENTION

1. Field of the Invention

The present invention relates generally to angiographic catheters used to access a blood vessel, and more particularly, to devices for sealing the external end of an angiographic catheter or needle following insertion of such devices into the vascular system.

2. Description of the Prior Art

Catheters and needles are inserted into the vascular system for many reasons including, diagnosis, therapy or to draw blood samples. During an angiographic procedure, a catheter is placed into the vascular system commonly using a Seldinger technique. This technique consists of placing a needle percutaneously into a blood vessel of the vascular system, and then threading a flexible guidewire through the lumen of the needle into the blood vessel. The guidewire is left in place within the blood vessel, and the needle is thereafter removed. The distal tip of the catheter is then threaded over the external end of the guidewire and advanced therealong and positioned within the vascular system in accordance with the prior placement of the guidewire; the guidewire is thereafter removed. Diagnostic fluids may then be injected into the blood vessel to diagnose or treat various vascular conditions.

The steps described above must often be repeated during a procedure in order to manipulate the catheter, i.e., to move the catheter into various branches of the vascular system. To perform such manipulation, the guidewire is reinserted into the catheter, and the guidewire and catheter are then manipulated to the new position.

The angiographic catheter includes a fluid-communicating lumen extending between the distal end and proximal end thereof. Upon introduction of the distal end of the catheter into the blood vessel, blood pressure within the body forces blood into the catheter lumen. Some blood may escape from the proximal end of the catheter even before the guidewire is removed by flowing through the annulus between the guidewire and the inner walls of the catheter. Once the guidewire is withdrawn from the catheter, the outward flow of blood through the lumen of the catheter is essentially unimpeded.

Physicians prefer to minimize the amount of blood leakage from angiographic catheters for two compelling reasons. First, it is important to prevent blood loss from the patient to avoid the need for blood transfusions. Secondly, blood may contain highly infectious material such as hepatitis or AIDS to which medical personnel are exposed, and it is therefore beneficial to medical personnel to limit blood loss.

In order to prevent blood from freely draining out of the angiographic catheter, a first port of a stopcock is commonly secured by means of a luer lock connection to the proximal end of the catheter external to the patient. Such stopcocks are well known and include a manually rotatable handle or lever operated by the thumb and forefinger for selectively opening or sealing the proximal end of the catheter. Such stopcocks typically include a second port, also provided with a luer lock connection fitting, in fluid communication with the first port thereof when the stopcock is open. In order to draw blood from the patient into a syringe, or to inject a substance into the blood vessel through the catheter, the stopcock must be turned by hand into the opened position. When the catheter is not being used to perform aspiration or infusion, it is standard medical practice to inject heparinized saline through the catheter while closing the stopcock. This anticoagulant solution flushes any blood from the catheter and thereafter prevents blood from entering the catheter and clotting inside.

As described above, during vascular procedures involving catheters, it is common to pass a guidewire into the proximal end of the catheter to help guide the catheter tip into a selected blood vessel. If a stopcock has been secured to the proximal end of the catheter, then the stopcock must first be opened so that the distal tip of the guidewire may be passed through the opened stopcock into the catheter. When the stopcock is opened, the heparinized saline that was previously injected into the catheter is flushed out by the blood. The guidewire is passed into the catheter which now contains stagnant blood which can form blood clots between the guidewire and the inner wall of the catheter. Moreover, during guidewire manipulations, the stopcock must be left open to permit passage of the guidewire; accordingly, blood can flow between the guidewire and inner lumen of the catheter, and often drips out at the second port of the stopcock. This slow flow of escaping blood may form clots within the catheter; these blood clots can be forced back into the vascular system when the guidewire is advanced or when subsequent injections are made through the catheter. Introduction of such blood clots can result in blocked blood vessels; if these blood vessels are critical, for example, the coronary arteries, it is possible that permanent, severe damage can occur.

Thus, while conventional stopcocks help to reduce the outflow of blood through angiographic catheters, they are only partially effective. Blood often flows out of a stopcock when opened for a guidewire to pass through it, or when a connection is made to a syringe or an infusion line. Moreover, conventional stopcocks are cumbersome because they often require two hands for operation. One hand holds the stopcock while the other turns the lever. This maneuver may be difficult for a physician to achieve, particularly when, for example, one of the physician's hands is needed to maintain the position of the catheter.

Another problem related to stopcocks arises when a catheter that has been fitted with a stopcock must be attached to a power injector, for example, when a large quantity of x-ray dye is to be injected while obtaining radiographs to visualize the blood vessel. The physician sometimes forgets to turn the stopcock into the opened position, in which case the dye is prevented from entering the catheter. The radiographs are obtained but do not provide the desired diagnostic information because the dye was not injected. The patient is therefore unnecessarily exposed to radiation, and the procedure must be repeated by the physician a second time to obtain the desired diagnostic information.

Apart from conventional stopcocks, other devices are known for reducing blood loss through angiographic catheters. For example, a variety of hemostasis valves are known which may be secured to the proximal end of an angiographic catheter to minimize blood loss around a guidewire that is positioned within a catheter, while permitting fluid to be injected into the catheter with the guidewire in place. One example of such a hemostasis valve is available from Cordis Corporation of Miami, Fla. under the product name "Adjustable Hemostasis Valve", Catalog No. 501-622. Such device includes a male luer lock connection fitting for being secured over the proximal end of an angiographic catheter. The device also includes a rotatable barrel which can be manually rotated to adjust the degree of compression exerted upon an annular compression washer. A guidewire may be inserted through the central opening in the rotatable barrel and passed into the proximal end of the catheter. The barrel can then be manually rotated to tighten the compression washer to form a seal about the guidewire. The device also includes a sideport extension with a luer lock fitting to permit flushing and/or infusion of fluids. However, such device must be manipulated by the physician to adjust the degree to which the compression washer seals against the walls of the guidewire. In addition, if the guidewire is to be removed, the device must again be manually rotated, first to release the guidewire, and thereafter to reseal the guidewire passage. As noted above, the physician's hands are often required for other purposes. A similar type of device is also available under the product name "Tuohy-Borst Adapter" from Universal Medical Instrument Corp. of Ballston Spa, New York; the latter device includes a sideport extension through which a high pressure injection of fluid may be made while the guidewire is clamped therein.

Another device which has been introduced to avoid leakage of blood from angiographic catheters is available from Medi-tech, Incorporated of Watertown, Mass. under the product name "FloSwitch HP" Catalog No. 44-200. This product resembles the device described within U.S. Pat. No. 4,243,034 issued to Brandt, and is further described in Widlus, "Technical Note: Safety of High Pressure Injections Through a Flow Switch Stopcock", *CardioVascular and Interventional Radiology* (1988) 11:307–308. The device includes a male luer connector at one end for being secured to the proximal end of the catheter, and includes an opposing end provided with a female luer connector for allowing a syringe to be secured thereto. The device includes a sliding thumb switch which may be opened or closed with or without a guidewire in place. If a guidewire is passed through such device, the slide switch may be advanced toward the closed position until the movable sealing member engages the wall of the guidewire to minimize blood leakage. While representing an improvement over a conventional stopcock or simple hemostasis valve, the "FloSwitch HP" flow control device still requires manual operation by the physician, and still allows a physician to forget that he has left the switch in the closed position when attempting to inject dye into the catheter.

Hemostasis valves using deformable elastomeric seals are widely known for use within catheter introducer sheaths. Such catheter introducer sheaths are available from a variety of manufacturers, including the catheter sheath introducer available from Cordis Corporation of Miami, Fla. under the product name "Catheter Sheath Introducer", Catalog No. 501-675U. Patents generally directed to such catheter introducer sheaths include U.S. Pat. No. 4,610,665 (Matsumoto et al.); U.S. Pat. No. 4,626,245 (Weinstein); U.S. Pat. No. 4,000,739 (Stevens); U.S. Pat. No. 4,430,081 (Timmermans); and U.S. Pat. No. 4,673,393 (Suzuki et al.). While such introducer sheaths are effective in preventing blood loss which would otherwise result when a catheter or guidewire is inserted therethrough, such devices do not solve the problem of preventing blood loss from the proximal end of an angiographic catheter of the type used to inject fluids under high pressure within the vascular system.

Finally, a variety of devices are known which include deformable elastomeric seals that are adapted to form a fluid seal but which are deformed upon insertion of the tip of a syringe or other conical member to permit fluid flow therethrough. Examples of such devices are described within U.S. Pat. No. 3,837,381 (Arroyo); U.S. Pat. No. 4,143,853 (Abramson); U.S. Pat. No. 4,387,879 (Tauschinski); U.S. Pat. No. 4,765,588 (Atkinson); U.S. Pat. No. 4,842,591 (Luther); and United Kingdom Patent No. 2,067,075 (Krutten et al.). In particular, the patent to Abramson describes a check valve for use with a catheter or needle and including a slit rubber disc supported in a housing having a first male connection having a standard luer-type taper and having a second luer-type female connection. The valve device is described for use in conjunction with a needle having a luer-type female fitting for withdrawing blood samples. Blood samples are withdrawn by inserting into the female connection of the check valve the tip of a syringe having a male connector at its tip to spread apart the slit in the valve. However, no suggestion is made in such disclosure of the use of such a check valve in conjunction with an angiographic catheter, or for passage of a guidewire therethrough.

The above-mentioned patent to Tauschinski discloses a self-sealing connector for coupling a vein catheter to a supply of blood or parenteral solution. The described device includes a slit elastic disc to selectively seal the flow of fluid. In at least one embodiment, an axially slidable member having a central bore is advanced into contact with the slit disc to open the same when the end of a supply hose is inserted into one of the ports of the device. Once again, no suggestion is made that such a device is capable of being used in conjunction with an angiographic catheter, that a guidewire be passed through the elastic disc, or that such a device is adapted for high pressure injections of fluid into an angiographic catheter.

The above-mentioned patent to Atkinson discloses a check valve for coupling a syringe to a fluid supply container for allowing a user to withdraw fluid from the supply container into the syringe. The check valve includes a slit elastomeric diaphragm. Insertion of the distal end of the syringe into the check valve causes such distal end to push through the slit diaphragm.

The above-mentioned patent to Luther describes a one-way valve connector for coupling a syringe tip to a catheter. The one-way valve includes a resilient slit septum that can be deformed by a movable plug. Insertion of the syringe tip causes the plug to move forwardly to deform the septum for allowing liquid to be injected therethrough. Again, no suggestion is made that such a check valve may be used with an angiographic catheter, or that a guidewire be passed through the slit of the resilient septum.

In addition, U.S. Pat. No. 3,601,151 to Winnard discloses a one way valve which, in one embodiment, is coupled between a needle inserted into a vein and a syringe used to withdraw blood samples. Such device does not include a slit seal and is not adapted to permit passage of a guidewire therethrough.

Accordingly, it is an object of the present invention to provide a device which can be secured to an angiographic catheter to prevent and/or minimize the loss of blood from the proximal end of such catheter following placement of the catheter within a blood vessel.

Another object of the present invention is to minimize blood loss from an angiographic catheter when inserting a guidewire therein.

Another object of the present invention is to provide such a device which permits a guidewire to be freely passed through an angiographic catheter while providing a seal around the guidewire to prevent any blood from passing between the guidewire and catheter while the guidewire is present.

Another object of the present invention is to prevent or minimize blood loss from an angiographic catheter when connecting or disconnecting a syringe or infusion line thereto.

Still another object of the present invention is to provide such a device which permits a syringe to be coupled to the proximal end of the catheter while effecting a fluid-tight, high-pressure seal therebetween.

Yet another object of the present invention is to provide such a device which does not require any manipulation of levers or switches in order to pass a guidewire into the proximal end of the catheter, and which similarly does not require any manipulation of levers or switches in order to inject or aspirate a fluid therethrough.

A further object of the present invention is to provide such a device which prevents heparinized saline or other anticoagulant fluid from being flushed out of the catheter when a syringe or fluid line is uncoupled from the proximal end of the catheter or when a guidewire is inserted into the catheter.

A still further object of the present invention to provide such a device which is of simple and inexpensive construction.

Another object of the present invention is to provide such a device which automatically opens when a syringe or other medical injection line is attached to it; similarly, when the syringe or injection line is removed therefrom, the device automatically closes without any intervention by the physician.

These and other objects of the invention will become more apparent to those skilled in the art as the description of the invention proceeds.

SUMMARY OF THE INVENTION

Briefly described, and in accordance with a preferred embodiment thereof, the present invention is a self-sealing valve device for use with angiographic catheters, and including a housing having a first end adapted to form a luer lock connection with the proximal end of the angiographic catheter for forming a fluid tight coupling therewith. The housing includes a second opposing end including a female luer lock connection fitting adapted to receive a complementary male luer lock connection fitting of a syringe, stopcock, or the like, to form a fluid tight connection therewith. The housing includes a central bore extending between the first and second opposing ends along a longitudinal axis of said housing. A deformable elastomeric seal is supported within the housing and extends across the central bore thereof to selectively seal the central bore. The deformable elastomeric seal includes a slit substantially aligned with the longitudinal axis of said housing to permit a guidewire to be passed therethrough while sealingly engaging the guidewire to prevent blood, heparinized saline, or other fluid within the catheter from passing beyond the deformable elastomeric seal.

As described above, the second end of the housing is provided with a female luer lock connection fitting for receiving a mating male luer lock connector. The self-sealing valve device of the present invention further includes a mechanism for deforming the aforementioned elastomeric seal automatically upon coupling of a male luer lock connection fitting to the second end of the housing in order to permit passage of blood or other fluids through the deformable elastomeric seal and through the central bore of the housing following connection of a syringe, stopcock, or the like, to the second end of the housing. In one embodiment of the present invention, this function is achieved by positioning the deformable elastomeric seal within the housing at a distance from the second end of the housing commensurate with the distance by which the conical tip of the syringe or other instrument extends into the second end of the housing for causing the conical tip of the syringe, stopcock, or the like, to directly contact and deform the deformable elastomeric seal in order to permit the passage of fluids therethrough. A guidance member may be provided for use in conjunction with such a device for guiding and supporting a guidewire to be passed through the slit of the deformable elastomeric seal.

In a second embodiment, the mechanism for deforming the elastomeric seal includes a depressor member supported within the housing for movement along the longitudinal axis of the housing between the seal and the second end of the housing. The depressor member has a central bore extending therethrough concentric with the longitudinal axis of the housing for permitting the passage of a guidewire or fluids therethrough. The depressor member has a first end disposed proximate the deformable elastomeric seal for contacting and deforming the seal when urged thereagainst. The depressor member also includes a second opposing end disposed proximate the second end of the housing and having an inwardly tapering conical surface for being abutted by the conical tip of a syringe, stopcock, or the like, connected to the second end of the housing. The insertion of the conical tip of the syringe, stopcock, or the like causes the depressor member to advance toward the deformable elastomeric seal to break the seal to permit fluids to pass therethrough. Preferably, the central bore of the housing includes a reduced-diameter portion proximate to the deformable elastomeric seal and disposed between said deformable elastomeric seal and the first end of the housing. The reduced-diameter portion provides a shoulder against which the deformable elastomeric seal rests when deformed, the shoulder thereby preventing excessive deformation of the deformable elastomeric seal.

Another aspect of the present invention relates to the incorporation of such a self-sealing valve device within the proximal end of an angiographic catheter as a unitary device ready for use.

Yet another aspect of the present invention is a method of performing an angiographic procedure using an angiographic catheter wherein the distal end of an angiographic catheter is placed within a blood vessel of a body and a deformable elastomeric seal having a slit formed therein is provided substantially adjacent the proximal end of the catheter to selectively seal the proximal end of the catheter against the loss of blood or other fluids therefrom. A fluid-tight coupling is then formed between the tip of a syringe and the proximal end of the catheter, while simultaneously deforming the deformable elastomeric seal to permit fluid to be passed therethrough or blood to be aspirated therethrough. Fluid is injected under pressure from the syringe through the deformable elastomeric seal and into the catheter for introducing the fluid under pressure into the body. The syringe is uncoupled from the proximal end of the catheter, while permitting the deformable elastomeric seal to return to its original position sealing the proximal end of the catheter. The step of providing the deformable elastomeric seal is preferably achieved by providing a housing having first and second opposing ends and including a central bore extending therebetween, supporting the deformable elastomeric seal within the housing and extending across the central bore, and forming a luer lock connection between a first end of the housing and the proximal end of the catheter. The step of forming a fluid-tight coupling between the tip of a syringe and the proximal end of the catheter is preferably achieved by forming a luer lock connection between the tip of the syringe and the second end of the housing.

The method of the present invention may also include the further step of inserting a guidewire through both the proximal end of the catheter and the slit of the deformable elastomeric seal, and passing the guide wire into the body through the catheter in order to position the guidewire within a blood vessel of the body.

BRIEF DESCRIPTION OF THE DRAWINGS

FIG. 1 is a perspective view of a self-sealing valve device for use with an angiographic catheter in accordance with the present invention, and further partially illustrates the proximal end of an angiographic catheter as well as the distal tip of a syringe.

FIG. 2 is a sectional view of the components shown in FIG. 1 viewed through the plane designated by arrows 2—2 as shown in FIG. 1.

FIG. 3 is a sectional view like that of FIG. 2 but directed to an alternate embodiment of the present invention, and including a guidance member for guiding a guidewire for passage through a deformable seal of the valve device.

FIG. 4 is a sectional view of the self-sealing valve device shown in FIG. 3 wherein the distal tip of a syringe engages and deforms the elastomeric seal of the valve device.

FIG. 5A illustrates a guidewire inserted within a blood vessel of a body.

FIG. 5B illustrates an angiographic catheter equipped with a self-sealing valve device being guided over the guidewire into the blood vessel.

FIG. 5C illustrates the guidewire being removed from the angiographic catheter.

FIG. 5D illustrates a syringe being coupled by a luer lock connection fitting with the self-sealing valve device for injecting fluid into the catheter.

FIG. 5E illustrates the syringe being detached from the valve device.

FIG. 5F illustrates the guidewire being passed into the valve device and through the catheter into the blood vessel.

FIG. 5G illustrates the angiographic catheter being removed from the guidewire.

DETAILED DESCRIPTION OF THE PREFERRED EMBODIMENTS

Figure 5A:
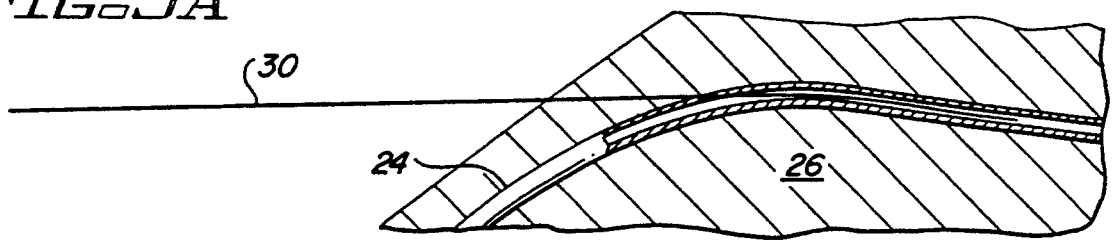
FIGS. 5A-5G illustrate steps of a method for performing an angiographic procedure.

Within FIG. 1, a self-sealing valve device, constructed in accordance with one embodiment of the present invention, is designated generally by reference numeral 10. Also shown in FIG. 1 is the proximal end 12 of an angiographic catheter 14, as well as the distal tip 16 of a syringe 18.

Figure 5B:
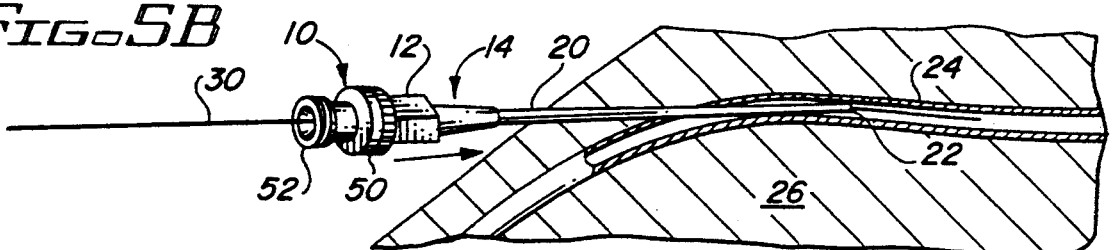

Before further describing self-sealing valve device 10, it will be helpful to first describe the structure of angiographic catheter 14. Catheter 14 includes a central, flexible shaft 20 which extends between proximal end 12 and an opposing distal end; this opposing distal end is visible within, for example, FIG. 5D and is designated therein by reference numeral 22. As indicated within FIG. 5D, distal end 22 of angiographic catheter 14 is adapted to be inserted into a blood vessel 24 of a patient's body 26. As indicated in FIGS. 1 and 2, a lumen 28 extends continuously through catheter 14 from proximal end 12 to distal end 22. Lumen 28 allows fluids to be passed through catheter 14, and also is adapted to receive a guidewire 30, as shown in FIG. 5B, to properly position catheter 14 within body 26.

Returning to FIGS. 1 and 2, proximal end 12 of angiographic catheter 14 includes a female luer lock connection fitting 32 which terminates in an annular sealing surface 34. Extending below sealing surface 34 is a cylindrical surface 36 upon which a single raised thread 38 is formed; raised thread 38 gradually spirals upwardly toward annular sealing surface 34. A reduced diameter cylindrical portion 40 couples female luer lock connection fitting 32 to squared portion 42, adapted to be grasped by a physician to steady catheter 14 when making or removing connections to luer lock connector 32. Conically tapered portion 44 of proximal end 12 joins with the upper end of shaft 20 of catheter 14.

As shown in FIGS. 1 and 2, female luer lock connector 32 of angiographic catheter 14 includes an inwardly converging conical bore 46 which extends through the center of annular sealing surface 34 and which communicates with lumen 28. Female luer lock connector 32 is adapted to receive a complimentary male luer lock connection fitting to form a fluid tight connection therewith; such a complimentary male luer lock connection fitting may be provided by, for example, distal end 16 of syringe 18, or by a port of a conventional stopcock, an infusion line, or the like. The features of angiographic catheter 14, including the structure of female luer lock connector 32 are well known in the art and do not form part of the present invention. However, an understanding of such features is helpful to an understanding the features of the present invention, which will now be described in greater detail.

Referring to FIGS. 1 and 2, self-sealing valve device 10 includes a housing 48, which is preferably molded from a medical-grade plastic similar to materials commonly used, for example, to mold proximal end 12 of catheter 14. Housing 48 includes a first end 50 and an opposing second end 52. A central bore 54 (see FIG. 2) extends continuously between first end 50 and second end 52 of housing 48 along longitudinal axis 56 of housing 48.

Second end 52 of housing 48 includes a female luer lock connection fitting 58 substantially identical in structure to female luer lock connector 32 described above in conjunction with the proximal end 12 of catheter 14. Female luer lock connector 58 includes an annular sealing surface 60, a raised spiral thread 62, and an inwardly converging conical bore 64 in fluid communication with central bore 54 of housing 48. Like female luer connector 32, female luer connector 58 is adapted to receive a complimentary male luer lock connection fitting of a syringe, stopcock, infusion line or the like, to form a fluid-tight connection therewith.

As shown in FIGS. 1 and 2, first end 50 of housing 48 includes a male luer lock connection fitting 66 adapted to be releasably secured with female luer lock connector 32 of catheter 14 in order to form a fluid-tight coupling therebetween. Male luer lock connector 66 includes a cylindrical extension 68 which preferably has a knarled outer surface, as shown in FIG. 1, for allowing a physician to more easily grip and rotate valve device 10 when securing the same to the proximal end 12 of catheter 14. As shown best in FIG. 2, cylindrical extension 68 is internally threaded for releasably receiving raised thread 38 of female luer lock connector 32. Male luer lock connector 50 further includes a conically-tapered tip portion 70 adapted to extend within conical bore 46 of female luer lock connector 32. The degree of taper of conical portion 70 is identical to that of conical bore 46 in order to effect a fluid-tight seal between male luer lock connector 50 and female luer lock connector 32 when such components are threaded together. Conical tip portion 70 includes a central bore 72 extending concentric with bore 54 for permitting fluids and/or a guidewire to be passed therethrough.

The male lock luer connector fitting 16 of syringe 18 essentially has the same features as those described immediately above for male lock luer connector 50. In particular, male luer lock connector 16 of syringe 18 includes a conically tapered tip portion 74 adapted to extend through, and sealingly engage, conical bore 64 of female luer lock connector 58.

As shown in FIG. 2, valve device 10 further includes a deformable elastomeric seal 76 supported within housing 48 and extending across central bore 54 thereof. Deformable elastomeric seal 76 includes a central slit formed therein substantially aligned with longitudinal axis 56 of housing 48. Deformable elastomeric seal 76 ordinarily extends continuously across the central bore within valve device 10 to selectively seal such central bore (see FIG. 3). The central slit formed within deformable elastomeric seal 76 permits a guidewire to be passed therethrough while sealingly engaging the walls of the guidewire to prevent blood or other fluids from passing around the guidewire through central bore 54. When the guidewire is removed, deformable elastomeric seal 76 returns to the closed position (see FIG. 3) for sealing the central bore of valve device 10. Those skilled in the art will appreciate that the Slit formed within deformable elastomeric seal 76 can be a single line slit or two or more slits which intersect one another proximate the center of elastomeric seal 76. Likewise, those skilled in the art will appreciate that deformable elastomeric seal 76 can comprise a single elastomeric disc or two or more slit elastomeric disks disposed one next to the other. In this regard, the reader is directed to the elastomeric seal structures shown in the aforementioned U.S. Pat. Nos. 4,387,879 (Tauschinski); 4,610,665 (Matsumoto et al.); 4,626,245 (Weinstein); and 4,673,393 (Suzuki et al.), the specifications and drawings of which patents are herein incorporated by reference. Those skilled in the art will appreciate that the term "deformable elastomeric seal", as used herein, is intend to include all such slit seal structures.

When syringe 18 is to be coupled to catheter 14 in order to inject or aspirate fluid, it is desirable that deformable elastomeric seal 76 be opened to facilitate the flow of fluid through valve device 10. In a first embodiment shown in FIG. 2, valve device 10 includes a depressor member 78 of generally cylindrical shape supported within central bore 54 of housing 48 for limited movement therein along longitudinal axis 56. As shown in FIG. 2, depressor member 78 is positioned between deformable elastomeric seal 76 and second end 52 of housing 48. Depressor member 78 has a central bore 80 formed therein of sufficient diameter to permit the passage of a guidewire, or the passage of fluid, therethrough. Central bore 80 of depressor member 78 is concentric with longitudinal axis 56 of housing 48. Depressor member 78 includes a generally bullet-shaped lower tip at a first end thereof, disposed proximate deformable elastomeric seal 76, for selectively contacting and deforming deformable elastomeric seal 76 when urged thereagainst, as shown in FIG. 2. Depressor member 78 also includes a second opposing end disposed proximate second end 52 of housing 48 and having an inwardly tapering conical surface for being abutted by conical tip 74 of syringe 18. As shown in FIG. 2, coupling of male luer lock connector 16 of syringe 18 to female luer connector 58 of housing 48 causes conical tip 74 of syringe 18 to push against depressor member 78, and thereby automatically cause deformable elastomeric seal 76 to open. When syringe 18 is removed from valve device 10, the natural resiliency of deformable elastomeric seal 76 urges depressor member 78 upwardly toward second end 52 of housing 48, thereby allowing elastomeric seal 76 to return its closed position (see FIG. 3). Thus, depressor member 78 serves as a means for deforming deformable elastomeric seal 76 upon coupling of a male luer lock connector to second end 52 of housing 48 in order to permit the passage of blood or other fluids through deformable elastomeric seal 76.

A second embodiment of the self-sealing valve device of the present invention is shown in FIGS. 3 and 4, and is designated generally by reference numeral 10'. Those features and components of valve device 10' which correspond with features described above in conjunction with valve device 10 are designated by like reference numerals. As shown in FIG. 3, no depressor member is required. Housing 48 of valve device 10' includes an inwardly tapering conical bore 64 that is continuous with central bore 54 of housing 48. In addition, deformable elastomeric seal 76 is supported much more closely to second end 52 of housing 48 as compared with valve device 10 shown in FIG. 2. As shown in FIG. 4, coupling of syringe 18 to second end 52 of valve device 10' causes conical tip 74 of syringe 18 to extend sufficiently within conical bore 64 to directly contact and deform deformable elastomeric seal 76. Deformable elastomeric seal 76 is supported within conical bore 54/64 at a distance from second end 52 corresponding to the distance by which conical tip 74 extends within second end 52. Accordingly, in this embodiment, no depressor member is required because the conical tip of the syringe, stopcock or other male luer lock connector device coupled to second end 52 directly contacts deformable elastomeric seal 76. Once syringe 18 is removed from valve device 10'; deformable elastomeric seal 76 returns to its closed position shown in FIG. 3.

Within valve device 10', deformable elastomeric seal 76 is supported within a circular recess 82 formed within conical bore 54/64. Thus, within the embodiment of the present invention shown in FIGS. 3 and 4, the circular recess 82 which supports deformable elastomeric seal 76 at a predetermined distance from second end 52 of housing 48 serves as a means for causing deformable elastomeric seal 76 to be deformed upon coupling of a male luer lock connector to second end 52 of housing 48.

Within the embodiment of the invention shown in FIG. 2, the inwardly tapering conical surface at the upper end of depressor member 78 aids in properly centering a guidewire being inserted through second end 52 of valve device 10. Depressor member 78 also helps to maintain the rigidity of the guidewire as it passes through and breaks the seal of deformable elastomeric seal 76. In contrast, valve device 10' shown in FIGS. 3 and 4 does not include a means for stiffening or centering a guidewire to facilitate passage of the guidewire through deformable elastomeric seal 76. Accordingly, as shown in FIG. 3, a guidance member 90 may be optionally used for such purpose. Guidance member 90 includes a conical tip 92 somewhat resembling the conical tip 74 of syringe 18. Guidance member 90 further includes a central bore 94, the diameter of which is somewhat greater adjacent upper end 96 then at the lower end of conical tip 92. The larger diameter opening adjacent upper end 96 facilitates the threading of the guidewire therethrough, while the reduced diameter portion extending through conical tip 92 helps to rigidify and center the distal tip of the guidewire directly over the slit portion of the deformable elastomeric seal 76. Conical tip 92 has a taper closely resembling the taper of conical bore 64 for causing central bore 94 to be substantially aligned with the longitudinal axis of housing 48 to guide the distal tip of the guidewire toward and through the slit formed within deformable elastomeric seal 76. After the distal tip of the guidewire is passed through deformable elastomeric seal 76, guidance member 90 may be removed by pulling guidance member 90 over the external (proximal) end of the guidewire.

The embodiments of the present invention described above with reference to FIGS. 1-4 contemplate self-sealing valve device 10 and 10' as components separate and apart from angiographic catheter 14. However, in a related aspect of the present invention, the self-sealing valve device may be integrally incorporated within the proximal end of an angiographic catheter, if desired. Essentially, this modification involves merging first end 50 of valve device 10 with proximal end 12 of angiographic catheter 14 to form an integral unified structure. Within such modified catheter structure, lumen 28 may essentially be continuous with central bore 72 of valve device 10. Such a modified form of angiographic catheter could be provided either using a depressor member 78, as shown in FIG. 2, or omitting such depressor member, as shown in FIGS. 3 and 4.

As indicated in FIG. 2, deformable elastomeric seal 76 may be supported within a circular recess 82 formed within the internal wall of central bore 54. Preferably, central bore 54 includes a reduced diameter portion 84 immediately below deformable elastomeric seal 76; reduced diameter portion 84 provides a shoulder against which deformable elastomeric seal 76 rests when deformed, thereby preventing excessive deformation of deformable elastomeric seal 76.

Another aspect of the present invention relates to the method of performing an angiographic procedure using an angiographic catheter in the manner described above. Such method is best described with reference to FIGS. 5A through 5G. In FIG. 5A, a guidewire 30 is shown after the distal portion thereof has been inserted percutaneously into a blood vessel 24 of a patient's body 26. Within FIG. 5B, the distal portion of catheter 14 is advanced over guidewire 30 into blood vessel 24, the distal end of catheter 14 being designated therein by reference numeral 22. As shown in FIG. 5B, valve device 10 has already been secured to the proximal end 12 of catheter 14, and guidewire 30 extends through the slit of the deformable elastomeric seal therein. Accordingly, no blood escapes from second end 52 of valve device 10 as catheter 14 is being placed within blood vessel 24.

Figure 5C:
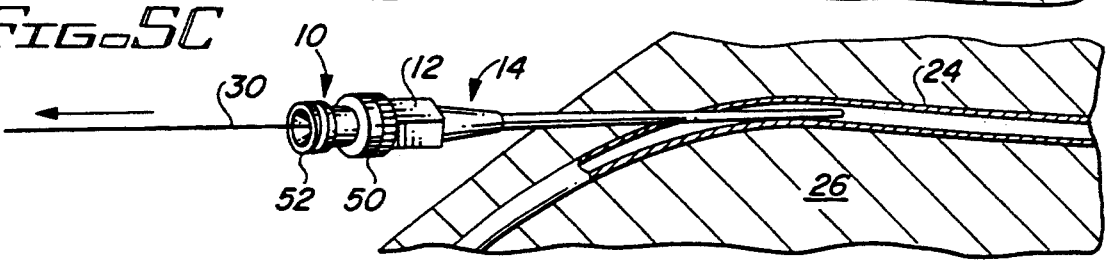

Having advanced catheter 14 to the desired point within blood vessel 24, guidewire 30 may then be removed, as indicated in FIG. 5C. As soon as guidewire 30 exits the deformable elastomeric seal within valve device 10, the seal returns to its closed position, preventing any loss of blood from second end 52 of valve device 10.

Figure 5D:
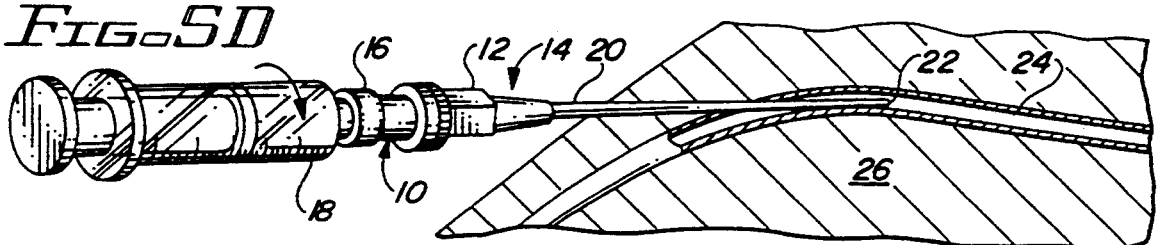
Figure 5E:
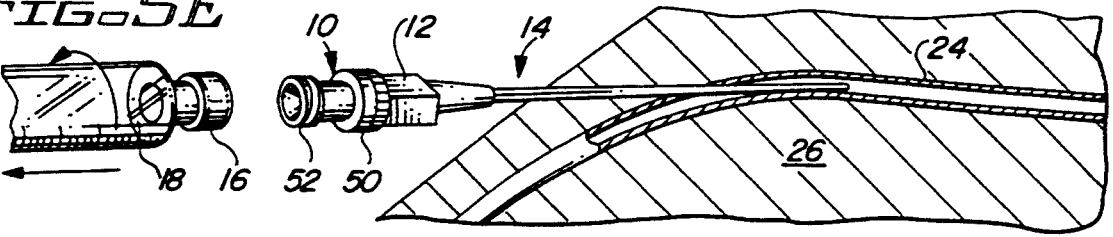

Turning to FIG. 5D, the male luer lock connector 16 of syringe 18 is secured over the female luer lock connector at the second end 52 of valve device 10 to form a fluid-tight coupling between the tip of the syringe and proximal end 12 of catheter 14. As explained above, this operation causes the deformable elastomeric seal to be deformed to permit fluid within syringe 18 to be injected into catheter 14. After injecting such fluid, for example, an angiographic dye used to perform diagnostic testing, syringe 18 is unthreaded from second end 52 of valve device 10. During this procedure the deformable elastomeric seal within valve device 10 returns to its closed position to prevent the escape of blood or other fluids within catheter 14.

Figure 5F:
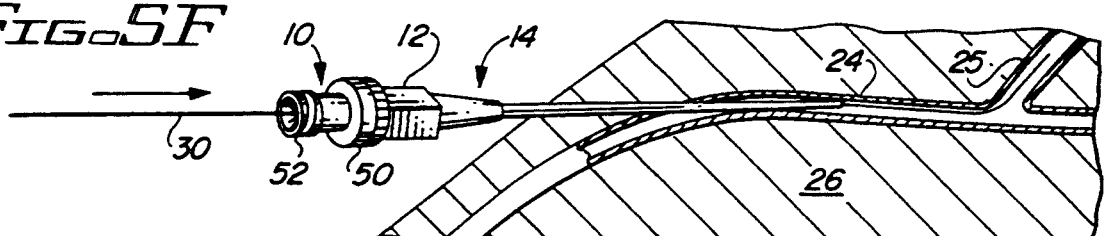
Figure 5G:
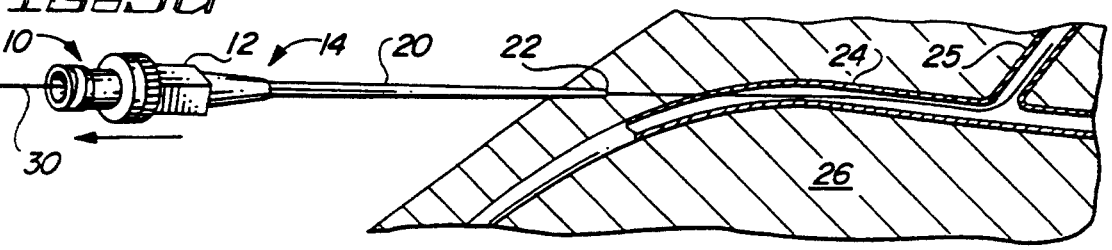

Such diagnostic testing may reveal that catheter 14 must be moved to a different portion of the vascular system, or perhaps, replaced with a different catheter. In this instance, guidewire 30 may be reinserted into valve device 10 and through catheter 14 in order to place the distal tip of guidewire 30 within a branch blood vessel 25, as shown in FIG. 5F. Again, the deformable elastomeric seal within valve device 10 enters into sealing engagement with the walls of guidewire 30 to prevent the passage of blood or other fluid out of second end 52 of valve device 10. If appropriate, catheter 14 may either be advanced over guidewire 30 to the branch vessel 25, or catheter 14 may be removed over guidewire 30, as shown in FIG. 5G, and be replaced with another catheter that is then passed over guidewire 30 into branch vessel 25.

Those skilled in the art will now appreciate that an improved self-sealing valve device has been described for use with angiographic catheters. The described valve device prevents or minimizes the loss of blood from the catheter when the catheter is inserted within the vascular system while permitting a guidewire to be freely passed into the catheter. The valve device does not require any levers, switches, or other manually operated components to open and close the seal therein, and automatically opens upon coupling of a syringe, infusion line, stopcock, or other medical instrument including a male luer lock connector as used herein, a syringe, infusion line, stopcock, or other medical instrument including a male luer connector are collectively referred to as fluid passage devices.

While the invention has been described with reference to preferred embodiments thereof, the description is for illustrative purposes only and is not to be construed as limiting the scope of the invention. Various modifications and changes may be made by those skilled in the art without departing from the true spirit and scope of the invention as defined by the appended claims.

I claim:

1. A self-sealing valve device for an angiographic catheter, the catheter including a distal end for insertion into a blood or lymph vessel of a patient and an opposing proximal end, the catheter including a lumen extending between the distal and proximal ends for passing fluids therethrough and for receiving a guide wire used to position the catheter with a blood or lymph vessel of a patient, the proximal end of the catheter including a female luer lock connection fitting adapted to receive a complementary male luer lock connection fitting of a syringe, stopcock, or other fluid passage device, to form a fluid tight connection therewith, said self-sealing valve device comprising in combination:

a) a housing having a central bore extending between first and second opposing ends of said housing along a longitudinal axis of said housing;

b) said first end of said housing including a male luer lock connection fitting for forming a fluid tight coupling with the female luer lock connection fitting at the proximal end of the catheter;

c) said second end of said housing including a female luer lock connection fitting adapted to receive a complementary male luer lock connection fitting of a syringe, stopcock, or other fluid passage device, to form a fluid tight connection therewith, said female luer lock connection fitting including an inwardly converging conical bore for receiving a conically-shaped tip of a syringe, stopcock, or other fluid passage device;

d) a deformable elastomeric seal supported within said housing and extending across the central bore thereof to selectively seal the central bore of said housing, said deformable elastomeric seal including at least one slit substantially aligned with the longitudinal axis of said housing to permit a guidewire to be passed therethrough while sealingly engaging the guidewire to prevent blood inside the catheter from passing beyond said deformable elastomeric seal; and e) means for deforming said deformable elastomeric seal upon coupling of a male luer lock connection fitting to said second end of said housing to permit passage of blood or other fluids through the deformable elastomeric seal and through the central bore of said housing following connection of a fluid passage device, to said second end of said housing, said deforming means being disposed within said housing proximate the second end thereof, said deforming means having a central bore formed therein, said central bore being substantially concentric with the longitudinal axis of said housing, said central bore having a diameter commensurate with the diameter of a guidewire to be passed through the catheter for centering the guidewire and for stiffening the guidewire as it passes through said deformable elastomeric seal.

2. The seal-sealing valve device for an angiographic catheter as recited by claim 1 including a guide wire extending through the central bore of said housing and into the proximal end of the catheter, said guidewire extending through said at least one slit of said deformable elastomeric seal, said deformable elastomeric seal sealingly engaging the guidewire to prevent blood inside the catheter from passing around said guidewire beyond said deformable elastomeric seal.

3. The seal-sealing valve device for an angiographic catheter as recited by claim 1 wherein the conical tip of the fluid passage device, extends for a predetermined length into said female luer lock connection fitting of said second end of said housing, and wherein said deforming means comprises means for positioning said deformable elastomeric seal within said housing at a distance from said second end of said housing of approximately said predetermined length for causing the conical tip of the fluid passage device, to directly contact and deform said deformable elastomeric seal in order to permit the passage of fluids therethrough.

4. The seal-sealing valve device for an angiographic catheter as recited by claim 3 further including a guidance member for facilitating passage of the distal tip of the guidewire through said at least one slit of said deformable elastomeric seal, said guidance member having a conical tip received by said second end of said housing, said conical tip of said guidance member including a bore extending therethrough commensurate in diameter with the diameter of the guidewire, the bore of said guidance member being substantially aligned with the longitudinal axis of said housing, and the conical tip of said guidance member extending proximate said deformable elastomeric seal for guiding the distal tip of a guidewire toward and through said at least one slit of said deformable elastomeric seal and into the catheter.

5. The seal-sealing valve device for an angiographic catheter as recited by claim 1 wherein said deforming means comprises a depressor member movably supported within said housing between said deformable elastomeric seal and second end of said housing, said depressor member having a central bore extending therethrough for permitting the passage of a guidewire or fluids therethrough, the central bore of said depressor member being concentric with the longitudinal axis of said housing, said depressor member being supported for movement along the longitudinal axis of said housing, said depressor member having a first end disposed proximate said deformable elastomeric seal for contacting and deforming said deformable elastomeric seal when urged thereagainst, said depressor member further including a second opposing end disposed proximate the second end of said housing and having an inwardly tapering conical surface for being abutted by the conical tip of the fluid passage device, connected to said second end of said housing, insertion of the conical tip of the fluid passage device causing said depressor member to advance toward said deformable elastomeric seal to break the seal to permit fluids to pass therethrough.

6. The seal-sealing valve device for an angiographic catheter as recited by claim 5 wherein the central bore of said housing includes a reduced-diameter portion proximate to said deformable elastomeric seal disposed between said deformable elastomeric seal and the first end of said housing, said reduced-diameter portion providing a shoulder against which said deformable elastomeric seal rests when deformed, said shoulder preventing excessive deformation of said deformable elastomeric seal.

7. An angiographic catheter having a self-sealing valve device, comprising in combination:
   a) an angiographic catheter including a distal end for insertion into a blood or lymph vessel of a patient and an opposing proximal end, said catheter including a lumen extending between the distal and proximal ends thereof along a longitudinal axis of said catheter for passing fluids therethrough and for receiving a guide wire used to position said catheter within a blood or lymph vessel of a patient, the proximal end of said catheter including a central passage concentric with said lumen, the proximal end of said catheter including a female luer lock connection fitting having an inwardly converging conical bore for receiving a conically-shaped tip of a fluid passage device and adapted to receive a complementary male luer lock connection fitting of such a syringe, stopcock, or other fluid passage device, to form a fluid tight connection therewith;
   b) a deformable elastomeric seal supported within the proximal end of said catheter and extending across the central passage thereof to selectively seal the central passage of the proximal end of said catheter, said deformable elastomeric seal including at least one slit substantially aligned with the longitudinal axis of said catheter to permit a guidewire to be passed therethrough while sealingly engaging the guidewire to prevent blood inside the lumen of said catheter from passing beyond said deformable elastomeric seal;
   c) means for deforming said deformable elastomeric seal upon coupling of a male luer lock connection fitting to said proximal end of said catheter to permit passage of blood or other fluids through the deformable elastomeric seal and through the lumen of said catheter following connection of the fluid passage device to said proximal end of said catheter, said deforming means being disposed within the proximal end of said catheter; and
   d) a guidance member for facilitating passage of the distal tip of the guidewire through said at least one slit of said deformable elastomeric seal, said guidance member extending within the proximal end of said catheter, said guidance member including a bore extending therethrough commensurate in diameter with the diameter of the guidewire, the bore of said guidance member being substantially aligned with the central passage of the proximal end of said catheter, and the bore of said guidance member extending proximate said deformable elastomeric seal for centering the guidewire and for stiffening the guidewire as it passes through said deformable elastomeric seal and into the lumen of said catheter, while permitting said deformable elastomeric seal to sealingly engage the guidewire.

8. The angiographic catheter having a self-sealing valve device as recited in claim 7 wherein the proximal end of said catheter terminates in an annular sealing surface, and wherein the conical tip of fluid passage device extends for a predetermined length into said female luer lock connection fitting of said proximal end of said catheter beyond said annular sealing surface, and wherein said deforming means comprises means for positioning said deformable elastomeric seal along the central passage of said proximal end of said catheter at a distance from said annular sealing surface of approximately said predetermined length for causing the conical tip of the fluid passage device to directly contact and deform said deformable elastomeric seal in order to permit the passage of fluids therethrough.

9. The angiographic catheter having a self-sealing valve device as recited in claim 7 including a guide wire extending into said lumen of said catheter and extending through the central passage of the proximal end of said catheter, said guidewire extending through said at least one slit of said deformable elastomeric seal, said deformable elastomeric seal sealingly engaging the guidewire to prevent blood inside the catheter from passing around said guidewire beyond said deformable elastomeric seal.

10. The angiographic catheter having a self-sealing valve device as recited in claim 7 wherein the proximal end of said catheter terminates in an annular sealing surface, and wherein said deforming means and said guide member jointly comprise a depressor member movably supported within the central passage of said proximal end of said catheter between said deformable elastomeric seal and said annular sealing surface, said depressor member having a central bore extending therethrough for permitting the passage of a guidewire or fluids therethrough, the central bore of said depressor member being concentric with the longitudinal axis of said catheter, said depressor member being supported for movement along the longitudinal axis of said catheter, said depressor member having a first end disposed proximate said deformable elastomeric seal for contacting and deforming said deformable elastomeric seal when urged thereagainst, said depressor member further including a second opposing end disposed proximate the annular sealing surface of said proximal end of said catheter and having an inwardly tapering conical surface for being abutted by the conical tip of the fluid passage device connected to said proximal end of said catheter, insertion of the conical tip of the fluid passage device causing said depressor member to advance toward said deformable elastomeric seal to break the seal to permit fluids to pass therethrough.

11. The angiographic catheter having a self-sealing valve device as recited in claim 10 wherein the central passage of said proximal end of said catheter includes a reduced-diameter portion proximate to said deformable elastomeric seal disposed between said deformable elastomeric seal and the lumen of said catheter, said reduced-diameter portion providing a shoulder against which said deformable elastomeric seal rests when deformed, said shoulder preventing excessive deformation of said deformable elastomeric seal.

12. An angiographic catheter and self-sealing valve device, comprising in combination:
   a) an angiographic catheter including a distal end for insertion into a blood or lymph vessel of a patient and an opposing proximal end, said catheter including a lumen extending between the distal and proximal ends for passing fluids therethrough and for receiving a guidewire used to position said catheter within a blood or lymph vessel of a patient, the proximal end of said catheter including a female luer lock connection fitting adapted to receive a complementary male luer lock connection fitting of a syringe, stopcock, or other fluid passage device, to form a fluid tight connection therewith;
   b) a housing having a central bore extending between first and second opposing ends of said housing along a longitudinal axis of said housing;
   c) said first end of said housing including a male luer lock connection fitting secured to said female luer lock connection fitting of said angiographic catheter for forming a fluid tight coupling with the female luer lock connection fitting at the proximal end of the catheter;

d) said second end of said housing including a female luer lock connection fitting adapted to receive a complementary male luer lock connection fitting of a syringe, stopcock, or other fluid passage device, to form a fluid tight connection therewith, said female luer lock connection fitting including an inwardly converging conical bore for receiving a conically-shaped tip of the fluid passage device;

e) a deformable elastomeric seal supported within said housing and extending across the central bore thereof to selectively seal the central bore of said housing, said deformable elastomeric seal including at least one slit substantially aligned with the longitudinal axis of said housing to permit a guidewire to be passed therethrough while sealingly engaging the guidewire to prevent blood inside the catheter from passing beyond said deformable elastomeric seal; and f) means for deforming said deformable elastomeric seal upon coupling of a male luer lock connection fitting to said second end of said housing to permit passage of blood or other fluids through the deformable elastomeric seal and through the central bore of said housing following connection of the fluid passage device, to said second end of said housing, said deforming means being disposed within said housing proximate the second end thereof, said deforming means having a central bore formed therein, said central bore being substantially concentric with the longitudinal axis of said housing, said central bore having a diameter commensurate with the diameter of a guidewire to be passed through the catheter for centering the guidewire and for stiffening the guidewire as it passes through said deformable elastomeric seal.

13. The apparatus as recited by claim 12 including a guide wire extending through the central bore of said housing and into the proximal end of the catheter, said guidewire extending through said at least one slit of said deformable elastomeric seal, said deformable elastomeric seal sealingly engaging the guidewire to prevent blood inside the catheter from passing around said guidewire beyond said deformable elastomeric seal.

14. The apparatus as recited by claim 12 wherein the conical tip of a syringe, stopcock, or other fluid passage device extends for a predetermined length into said female luer lock connection fitting of said second end of said housing, and wherein said deforming means comprises means for positioning said deformable elastomeric seal within said housing at a distance from said second end of said housing of approximately said predetermined length for causing the conical tip of the fluid passage device, to directly contact and deform said deformable elastomeric seal in order to permit the passage of fluids therethrough.

15. The apparatus as recited by claim 14 further including a guidance member for facilitating passage of the distal tip of the guidewire through said at least one slit of said deformable elastomeric seal, said guidance member having a conical tip received by said second end of said housing, said conical tip of said guidance member including a bore extending therethrough commensurate in diameter with the diameter of the guidewire, the bore of said guidance member being substantially aligned with the longitudinal axis of said housing, and the conical tip of said guidance member extending proximate said deformable elastomeric seal for guiding the distal tip of a guidewire toward and through said at least one slit of said deformable elastomeric seal and into said catheter.

16. The apparatus as recited by claim 12 wherein said deforming means comprises a depressor memory movably supported within said housing between said deformable elastomeric seal and second end of said housing, said depressor member having a central bore extending therethrough for permitting the passage of a guidewire or fluids therethrough, the central bore of said depressor member being concentric with the longitudinal axis of said housing, said depressor member being supported for movement along the longitudinal axis of said housing, said depressor member having a first end disposed proximate said deformable elastomeric seal for contacting and deforming said deformable elastomeric seal when urged thereagainst, said depressor member further including a second opposing end disposed proximate the second end of said housing and having an inwardly tapering conical surface for being abutted by the conical tip of a fluid passage device, connected to said second end of said housing, insertion of the conical tip of the fluid passage device causing said depressor member to advance toward said deformable elastomeric seal to break the seal to permit fluids to pass therethrough.

17. The apparatus as recited by claim 16 wherein the central bore of said housing includes a reduced-diameter portion proximate to said deformable elastomeric seal disposed between said deformable elastomeric seal and the first end of said housing, said reduced-diameter portion providing a shoulder against which said deformable elastomeric seal rests when deformed, said shoulder preventing excessive deformation of said deformable elastomeric seal.

18. An angiographic catheter having a self-sealing valve device, comprising in combination:

a) an angiographic catheter including a distal end for insertion into a blood or lymph vessel of a patient and an opposing proximal end, said catheter including a lumen extending between the distal and proximal ends thereof along a longitudinal axis of said catheter for passing fluids therethrough and for receiving a guide wire used to position said catheter within a blood or lymph vessel of a patient, the proximal end of said catheter including a central passage concentric with said lumen, the proximal end of said catheter including a female luer lock connection fitting having an inwardly converging conical bore for receiving a conically-shaped tip of a fluid passage device and adapted to receive a complementary male luer lock connection fitting of such a fluid passage device, to form a fluid tight connection therewith;

b) a deformable elastomeric seal supported within the proximal end of said catheter and extending across the central passage thereof to selectively seal the central passage of the proximal end of said catheter, said deformable elastomeric seal including at least one slit substantially aligned with the longitudinal axis of said catheter to permit a guidewire to be passed therethrough while sealingly engaging the guidewire to prevent blood inside the lumen of said catheter from passing beyond said deformable elastomeric seal;

c) means for deforming said deformable elastomeric seal upon coupling of a male luer lock connection fitting to said proximal end of said catheter to permit passage of blood or other fluids through the deformable elastomeric seal and through the lumen of said catheter following connection of the fluid passage device to said proximal end of said catheter, said deforming means being disposed within the proximal end of said catheter, said central bore being substantially concentric with the longitudinal axis of said housing, said central bore having a diameter commensurate with the diameter of a guidewire to be passed through said catheter for centering the guidewire and for stiffening the guidewire as it passes through said deformable elastomeric seal.

19. A self-sealing valve device for an angiographic catheter, the catheter including a distal end for insertion into a blood or lymph vessel of a patient and an opposing proximal end, the catheter including a lumen extending between the distal and proximal ends for passing fluids therethrough and for receiving a guide wire used to position the catheter within a blood or lymph vessel of a patient, the proximal end of the catheter including a female luer lock connection fitting adapted to receive a complementary male luer lock connection fitting of a syringe, stopcock, or other fluid passage device, to form a fluid tight connection therewith, said self-sealing valve device comprising in combination:

a) a housing having a central bore extending between first and second opposing ends of said housing along a longitudinal axis of said housing;
b) said first end of said housing including a male luer lock connection fitting for forming a fluid tight coupling with the female luer lock connection fitting at the proximal end of the catheter;
c) said second end of said housing including a female luer lock connection fitting adapted to receive a complementary male luer lock connection fitting of a fluid passage device, to form a fluid tight connection therewith, said female luer lock connection fitting including an inwardly converging conical bore for receiving a conically-shaped tip of the fluid passage device;
d) a deformable elastomeric seal supported within said housing and extending across the central bore thereof to selectively seal the central bore of said housing, said deformable elastomeric seal including at least one slit substantially aligned with the longitudinal axis of said housing to permit a guidewire to be passed therethrough while sealingly engaging the guidewire to prevent blood inside the catheter from passing beyond said deformable elastomeric seal; and
e) means for deforming said deformable elastomeric seal upon coupling of a male luer lock connection fitting to the proximal end of the catheter to permit passage of blood or other fluids through the deformable elastomeric seal and through the lumen of said catheter following connection of the fluid passage device to said proximal end of said catheter, said deforming means being disposed within the proximal end of said catheter; and
f) a guidance member for facilitating passage of the distal tip of the guidewire through said at least one slit of said deformable elastomeric seal, said guidance member extending within the proximal end of said catheter, said guidance member including a bore extending therethrough commensurate in diameter with the diameter of the guidewire, the bore of said guidance member being substantially aligned with the central passage of the proximal end of said catheter, and the bore of said guidance member extending proximate said deformable elastomeric seal for centering the guidewire and for stiffening the guidewire as it passes through said deformable elastomeric seal and into the lumen of said catheter, while permitting said deformable elastomeric seal to sealingly engage the guidewire.

20. An angiographic catheter and self-sealing valve device, comprising in combination:

a) an angiographic catheter including a distal end for insertion into a blood or lymph vessel of a patient and an opposing proximal end, said angiographic catheter including a lumen extending between the distal and proximal ends for passing fluids therethrough and for receiving a guidewire used to position said catheter within a blood or lymph vessel of a patient, the proximal end of said catheter including a female luer lock connection fitting adapted to receive a complementary male luer lock connection fitting of a fluid passage device, to form a fluid tight connection therewith;
b) a housing having a central bore extending between first and second opposing ends of said housing along a longitudinal axis of said housing;
c) said first end of said housing including a male luer lock connection fitting secured to said female luer lock connection fitting of said angiographic catheter for forming a fluid tight coupling with the female luer lock connection fitting at the proximal end of the catheter;
d) said second end of said housing including a female luer lock connection fitting adapted to receive a complementary male luer lock connection fitting of the fluid passage device, to form a fluid tight connection therewith, said female luer lock connection fitting including an inwardly converging conical bore for receiving a conically-shaped tip of the fluid passage device;
e) a deformable elastomeric seal supported within said housing and extending across the central bore thereof to selectively seal the central bore of said housing, said deformable elastomeric seal including at least one slit substantially aligned with the longitudinal axis of said housing to permit a guidewire to be passed therethrough while sealingly engaging the guidewire to prevent blood inside the catheter from passing beyond said deformable elastomeric seal;
f) means for deforming said deformable elastomeric seal upon coupling of a male luer lock connection fitting to the proximal end of the catheter to permit passage of blood or other fluids through the deformable elastomeric seal and through the lumen of said catheter following connection of the fluid passage device to the proximal end of said catheter, said deforming means being disposed within the proximal end of said catheter; and
g) a guidance member for facilitating passage of the distal tip of the guidewire through said at least one slit of said deformable elastomeric seal, said guidance member extending within the proximal end of said catheter, said guidance member including a bore extending therethrough commensurate in diameter with the diameter of the guidewire, the bore of said guidance member being substantially aligned with the central passage of the proximal end of the catheter, and the bore of said guidance member extending proximate said deformable elastomeric seal for guiding the distal tip of a guidewire toward and through said at least one slit of said deformable elastomeric seal and into the lumen of the catheter, while permitting said deformable elastomeric seal to sealingly engage the guidewire.

* * * * *